US007258871B2

(12) United States Patent
Horowski et al.

(10) Patent No.: US 7,258,871 B2
(45) Date of Patent: Aug. 21, 2007

(54) COMBINATION OF A TRANSDERMAL THERAPEUTIC SYSTEM AND AN ORAL AND/OR PARENTERAL PREPARATION CONTAINING DOPAMINE AGONISTS FOR THE TREATMENT OF DOPAMINERGIC DISEASE STATES

(75) Inventors: Reinhard Horowski, Berlin (DE); Johannes Tack, Berlin (DE)

(73) Assignee: Neurobiotec GmbH, Berlin (DE)

( * ) Notice: Subject to any disclaimer, the term of this patent is extended or adjusted under 35 U.S.C. 154(b) by 330 days.

(21) Appl. No.: 10/362,182

(22) PCT Filed: Aug. 24, 2001

(86) PCT No.: PCT/EP01/09826

§ 371 (c)(1),
(2), (4) Date: Jul. 3, 2003

(87) PCT Pub. No.: WO02/34267

PCT Pub. Date: May 2, 2002

(65) Prior Publication Data

US 2004/0092544 A1 May 13, 2004

(30) Foreign Application Priority Data

Oct. 20, 2000 (DE) ................. 100 53 397

(51) Int. Cl.
*A61K 9/70* (2006.01)
*A61K 9/00* (2006.01)
*A61K 9/20* (2006.01)
*A61K 9/48* (2006.01)

(52) U.S. Cl. ............... 424/443; 424/400; 424/447; 424/448; 424/451; 424/464

(58) Field of Classification Search ............... 424/400, 424/443, 447, 448, 464, 451
See application file for complete search history.

(56) References Cited

U.S. PATENT DOCUMENTS

| | | | |
|---|---|---|---|
| 3,953,454 A | 4/1976 | Zikan et al. | |
| 3,954,988 A * | 5/1976 | Itil et al. | .......... 514/288 |
| 4,166,182 A | 8/1979 | Kornfeld et al. | |
| 4,202,979 A | 5/1980 | Kornfeld et al. | |
| 4,299,836 A | 11/1981 | Karacsony et al. | |
| 4,379,790 A | 4/1983 | Horowski et al. | |
| 4,673,681 A | 6/1987 | Poli | |
| 4,742,054 A | 5/1988 | Naftchi | |
| 4,797,405 A | 1/1989 | Conine et al. | |
| 4,798,834 A | 1/1989 | Merritt et al. | |
| 4,800,204 A | 1/1989 | Mueller | |
| 4,935,429 A | 6/1990 | Dackis et al. | |
| 4,968,801 A | 11/1990 | Sauer et al. | |
| 4,970,200 A | 11/1990 | Birkmayer et al. | |
| 5,057,321 A | 10/1991 | Edgren et al. | |
| 5,071,657 A | 12/1991 | Oloff et al. | |
| 5,114,948 A | 5/1992 | Conine et al. | |
| 5,190,763 A | 3/1993 | Edgren et al. | |
| 5,192,550 A | 3/1993 | Edgren et al. | |
| 5,221,536 A | 6/1993 | Edgren et al. | |
| 5,229,129 A * | 7/1993 | Chiang | ............ 424/449 |
| 5,252,335 A | 10/1993 | Chiang | |
| 5,364,628 A | 11/1994 | Kissel et al. | |
| 5,371,000 A | 12/1994 | Hummel-Maquardt et al. | |
| 5,378,730 A | 1/1995 | Lee et al. | |
| 5,399,355 A * | 3/1995 | Riedl et al. | ............ 424/448 |
| 5,462,744 A | 10/1995 | Gupte et al. | |
| 5,593,686 A | 1/1997 | Kissel et al. | |
| 5,597,832 A | 1/1997 | Michaelides et al. | |
| 5,607,691 A | 3/1997 | Hale et al. | |
| 5,643,586 A | 7/1997 | Perricone | |
| 5,650,420 A | 7/1997 | Hall et al. | |
| 5,656,286 A | 8/1997 | Miranda et al. | |
| 5,674,875 A | 10/1997 | Cohen | |
| 5,679,685 A | 10/1997 | Cincota et al. | |
| 5,696,125 A | 12/1997 | Altura et al. | |
| 5,696,128 A | 12/1997 | Cincotta et al. | |
| 5,728,378 A | 3/1998 | Hellstrand et al. | |
| 5,738,869 A | 4/1998 | Fischer et al. | |

(Continued)

FOREIGN PATENT DOCUMENTS

| | | |
|---|---|---|
| DE | 41 16 912 | 11/1992 |
| DE | 42 40 798 | 6/1993 |
| DE | 196 26 621 | 1/1998 |
| DE | 199 38 823 | 2/2001 |
| DE | 100 54 713 | 7/2001 |
| DE | 100 43 321 | 3/2002 |

(Continued)

OTHER PUBLICATIONS

Von Haut and Blutentraumen, "LTS Lohmann Therapie-Systeme" Leben braucht Visionen, Nov. 21, 1997.
Gurny, Dr. Robert, et al., "Dermal and Transdermal Drug Delivery" New Insights and Perspectives, Second International Symposium of the International Association for Pharmaceutical Technology (APV) Frankfurt, Nov. 11-13, 1991, Wissenschaftliche Velagsgesellschaft mbH Stuttgart (1993).

(Continued)

*Primary Examiner*—Michael G. Hartley
*Assistant Examiner*—Simon J. Oh
(74) *Attorney, Agent, or Firm*—Pillsbury Winthrop Shaw Pittman LLP

(57) ABSTRACT

The invention relates to the use of a dopamine agonist in the form of an agent consisting of at least two spatially discrete compositions, of which one is a transdermal therapeutic system (TTS) containing the dopaminergic agent and another one or more are preparations for oral and/or parenteral application containing that same dopaminergic agent for the treatment of dopaminergically treatable diseases with the following elements: a) the TTS is continuously applied, b) within the duration of application in a) the composition for oral or parenteral dosage is administered.

36 Claims, No Drawings

U.S. PATENT DOCUMENTS

| | | | |
|---|---|---|---|
| 5,830,505 A | 11/1998 | Fischer et al. |
| 5,849,800 A | 12/1998 | Smith |
| 5,858,410 A | 1/1999 | Muller et al. |
| 5,872,145 A | 2/1999 | Plachetka |
| 5,877,183 A | 3/1999 | Cincotta |
| 5,902,815 A | 5/1999 | Olney et al. |
| 5,994,363 A | 11/1999 | El-Rashidy et al. |
| 6,001,390 A | 12/1999 | Yum et al. |
| 6,001,861 A | 12/1999 | Oertel et al. |
| 6,114,326 A | 9/2000 | Schueler |
| 6,187,756 B1 | 2/2001 | Lee et al. |
| 6,191,132 B1 | 2/2001 | Klockgether et al. |
| 6,217,905 B1 | 4/2001 | Edgren et al. |
| 6,221,870 B1 | 4/2001 | Pfaeffli |
| 6,299,900 B1 | 10/2001 | Reed et al. |
| 6,348,208 B1 | 2/2002 | Blume et al. |
| 6,380,208 B2 | 4/2002 | Dib et al. |
| 6,380,267 B1 | 4/2002 | Swope |
| 6,384,083 B1 | 5/2002 | Ludwig et al. |
| 6,388,079 B1 | 5/2002 | Wu et al. |
| 6,391,871 B1 | 5/2002 | Olney et al. |
| 6,395,901 B1 | 5/2002 | Mangia et al. |
| 6,461,636 B1 | 10/2002 | Arth et al. |
| 6,500,857 B1 | 12/2002 | Perricone et al. |
| 6,503,920 B1 | 1/2003 | Gomez-Mancilla |
| 6,514,482 B1 | 2/2003 | Bartus et al. |
| 6,562,365 B2 | 5/2003 | Blume et al. |
| 6,572,879 B1 | 6/2003 | Yum et al. |
| 6,576,671 B1 | 6/2003 | Bongrani et al. |
| 6,602,868 B2 | 8/2003 | McBrinn et al. |
| 6,613,507 B1 | 9/2003 | Chang |
| 6,620,429 B1 | 9/2003 | Muller |
| 6,623,752 B1 | 9/2003 | Fischer et al. |
| 6,632,217 B2 | 10/2003 | Harper et al. |
| 6,673,806 B2 | 1/2004 | Tomasi et al. |
| 6,680,327 B2 | 1/2004 | Candiani et al. |
| 6,685,959 B1 | 2/2004 | Moreau et al. |
| 6,689,118 B2 | 2/2004 | Alchas et al. |
| 6,699,495 B2 | 3/2004 | Blume et al. |
| 6,699,498 B1 | 3/2004 | Muller |
| 6,713,493 B2 | 3/2004 | Dib et al. |
| 6,716,854 B2 | 4/2004 | McBrinn et al. |
| 6,727,363 B2 | 4/2004 | Tomasi et al. |
| 6,770,638 B2 | 8/2004 | Fick et al. |
| 6,800,635 B2 | 10/2004 | Tomasi et al. |
| 6,818,226 B2 | 11/2004 | Reed et al. |
| 2001/0053777 A1 | 12/2001 | Brecht |
| 2002/0009486 A1 | 1/2002 | Godbey |
| 2002/0013332 A1 | 1/2002 | Dib et al. |
| 2002/0019421 A1 | 2/2002 | Biberman |
| 2002/0068092 A1 | 6/2002 | Bosch et al. |
| 2002/0110585 A1 | 8/2002 | Godbey et al. |
| 2002/0123503 A1 | 9/2002 | Ross et al. |
| 2002/0132827 A1 | 9/2002 | Nichols et al. |
| 2002/0193758 A1 | 12/2002 | Sandberg |
| 2002/0193778 A1 | 12/2002 | Alchas et al. |
| 2003/0026830 A1 | 2/2003 | Lauterback et al. |
| 2003/0108611 A1 | 6/2003 | Bosch et al. |
| 2003/0114476 A1 | 6/2003 | Plachetka et al. |
| 2003/0166709 A1 | 9/2003 | Rimpler et al. |
| 2003/0181462 A1 | 9/2003 | Doods et al. |
| 2003/0212065 A1 | 11/2003 | McBrinn et al. |
| 2004/0013620 A1 | 1/2004 | Klose et al. |
| 2004/0028723 A1 | 2/2004 | Horowski et al. |
| 2004/0048779 A1 | 3/2004 | Schollmayer |
| 2004/0081683 A1 | 4/2004 | Schacht et al. |
| 2004/0087596 A1 | 5/2004 | Schneider |
| 2004/0092544 A1 | 5/2004 | Horowski et al. |
| 2004/0092744 A1 | 5/2004 | Tomasi et al. |
| 2004/0096491 A1 | 5/2004 | Tateishi et al. |
| 2004/0101550 A1 | 5/2004 | Windt-Hanke et al. |
| 2004/0102652 A1 | 5/2004 | Amari et al. |
| 2004/0105889 A1 | 6/2004 | Ryde et al. |
| 2004/0120995 A1 | 6/2004 | Martin et al. |
| 2004/0137045 A1 | 7/2004 | Breitenbach et al. |
| 2004/0138235 A1 | 7/2004 | Grzelak et al. |
| 2004/0147581 A1 | 7/2004 | Taylor et al. |
| 2004/0166159 A1 | 8/2004 | Han et al. |
| 2004/0170654 A1 | 9/2004 | Pinkerton |
| 2004/0170672 A1 | 9/2004 | Selzer |
| 2004/0180904 A1 | 9/2004 | Beck |
| 2004/0209861 A1 | 10/2004 | Benavides et al. |
| 2004/0209909 A1 | 10/2004 | Yum et al. |
| 2004/0209910 A1 | 10/2004 | Gutman et al. |
| 2004/0213816 A1 | 10/2004 | Weiner et al. |
| 2004/0219191 A1 | 11/2004 | Kuhn |
| 2004/0241240 A1 | 12/2004 | Terahara et al. |
| 2004/0247656 A1 | 12/2004 | Beier et al. |
| 2004/0253299 A1 | 12/2004 | Beier et al. |
| 2005/0031667 A1 | 2/2005 | Patel et al. |

FOREIGN PATENT DOCUMENTS

| | | |
|---|---|---|
| EP | 0 137 278 | 8/1984 |
| EP | 0 155 229 | 2/1985 |
| EP | 0 056 358 | 4/1987 |
| EP | 0 314 387 | 10/1988 |
| EP | 0 458 640 | 5/1991 |
| EP | 0428 038 | 5/1991 |
| EP | 0458 640 | 11/1991 |
| EP | 1 027 889 | 5/1992 |
| EP | 738 513 | 10/1996 |
| EP | 0526566 | 11/1998 |
| EP | 0737066 | 4/2003 |
| EP | 0910379 | 4/2003 |
| EP | 1444977 | 8/2004 |
| GB | 1 526 835 | 10/1978 |
| WO | WO89/04179 | 5/1989 |
| WO | WO91/00746 | 1/1991 |
| WO | WO92/14453 | 9/1992 |
| WO | WO92/20339 | 11/1992 |
| WO | WO96/39136 | 12/1996 |
| WO | WO97/11696 | 4/1997 |
| WO | WO99/48484 | 9/1999 |
| WO | WO99/49853 | 10/1999 |
| WO | WO 01/28555 | 4/2001 |
| WO | PCT/EP01/09823 | 8/2001 |
| WO | PCT/EP01/09824 | 8/2001 |
| WO | PCT/EP01/09826 | 8/2001 |
| WO | WO 01/72291 | 10/2001 |
| WO | WO 02/15890 | 2/2002 |
| WO | 02/34267 | 5/2002 |
| WO | WO 02/069941 | 9/2002 |
| WO | WO 02/078602 | 10/2002 |
| WO | WO 02/087508 | 11/2002 |
| WO | WO 02/102424 | 12/2002 |
| WO | WO 2004/032900 | 4/2004 |
| WO | PCT/DE2004/001133 | 5/2004 |
| WO | WO 2004/082630 | 9/2004 |
| WO | WO 2004/089375 | 10/2004 |
| WO | WO 2005/025546 | 3/2005 |

OTHER PUBLICATIONS

"Rote Liste" 1999 No. 76111 Estracomb TTS®, Rote Liste® Service GmbH, Frankfurt/Main.

Den Daas et al.: "Transdermal administration of the dopamine agonist N-0437 and seven ester prodrugs: comparison with oral administration in the 6-OHDA turning model", Naunyn-Schmiedeberg's Arch Pharmacol 342:655-659 (1990).

Abstract from Eur. J. Clin. Pharmacol. 41, 17-21, 1991.

International Search Report of PCT/EP2006/002093 dated Aug. 31, 2006, 8 pages.

Written Opinion of the International Searching Authority in PCT/EP20026/002093 dated Aug. 31, 2006, 8 pages.

Database Biosis, XP002393041, vol. 58, No. 5, "Cabergoline can increase penile erections and libido", Mar. 12, 2002, 3 pages.

Database Medline, XP002393147, Horvath et al., "Severe multivalvular heart disease: a new complication of the ergot derivative dopamine agonists.", Official Journal of the Movement Disorder Society, vol. 19, No. 6, Jun. 2004, Abstract, 1 page.

* cited by examiner

COMBINATION OF A TRANSDERMAL THERAPEUTIC SYSTEM AND AN ORAL AND/OR PARENTERAL PREPARATION CONTAINING DOPAMINE AGONISTS FOR THE TREATMENT OF DOPAMINERGIC DISEASE STATES

The invention relates to the use of a means including a transdermal therapeutic system (TTS) containing a dopamine agonist for treating dopaminergic disease states under a special treatment plan.

A TTS containing lisuride is known from publication WO 91/00746. Diseases for which a dopamine therapy is indicated such as Parkinson's disease are severe chronic and disabling diseases from which older and polymorbid patients suffer frequently. The state-of-the-art practice is oral administration of a combination of dopaminergic substances. These generally include various formulations of levodopa (high initial flux rate, normal or slow release), levodopa boosters such as decarboxylase inhibitors as the base and optionally COMT inhibitors or MAO-B inhibitors, and various dopamine agonists such as bromocriptine, lisuride, cabergoline, pergolide, ropinirole, pramipexole as well as amantadines and, occasionally, anticholinergic agents. The pharmacokinetics of fast-acting levodopa is hard to control for various reasons, and dopamine agonists frequently do not allow safe bioavailability and thus efficacy predictions. All these active agents also can interact for pharmacological and pharmacokinetic reasons, in addition to their interaction with other active agents or pharmaceuticals that older patients with multiple diseases frequently need.

Either a continuous or a discontinuous stimulation may be required depending on the stage of the disease and the actual status of the patient. A good foundation is laid when the level of dopaminergic agents is kept stable across the entire day. However patients frequently report that they often need to take a fast-acting dopaminergic agent at certain times of the day to overcome acute motoric disturbances, severe and painful dystonia, etc. ("kick"). In extreme cases, such sudden "off" states of motoric performance and akinesia (sometimes predictable early in the morning or afternoon, but frequently all of the sudden and unexpectedly) can only be controlled with injectable active agents such as apomorphine. On the other hand, strong and fast efficacy hikes can cause disturbing side effects (e.g. nausea, emesis, orthostatic hypotension, narcoleptic attacks). Overdoses due to the narrow therapeutic time window of all these dopaminergic agents can result in severe dyskinesia, dystonia or, especially in older patients, psychoses. The latter severe problem is mainly connected with high active agent concentrations in the plasma over night that are known to destroy regular sleeping patterns and to prevent the REM sleep phase (with REM rebound during daytime as indication of a psychosis).

Because of the interrelations described, a practical dopamine treatment is started at very low doses of one or several active agents with subsequent, for example, weekly, dose increases until side effects indicate bioavailability. After a subsequent and rather arbitrary reduction of the dose or dose stabilization, the next active agent is administered and set or dosed ("titrated") accordingly. As a result, treatment plans and most of all dosages vary considerably depending on the severity of the disease, the patient's individual body constitution and metabolization type. Mostly 3 or more different active agents are administered orally. A typical patient would for example start with fast-acting levodopa in the morning, followed by a dose of MAO-B inhibitor and, throughout the day, four or five doses of normally acting levodopa in combination with a dopamine agonist and, eventually, a slow-acting preparation containing levodopa (or a low dose of a long-term acting dopamine agonist) at bedtime ensuring sufficient mobility in the sleep and consequently a high relaxation value.

Such a complicated treatment plan is more often the rule than an exception and is not very well compatible, especially not with older patients, is unstable and sensitive to interaction with other factors such as other agents administered or infection-related diseases as well as dehydration by inadequate fluid intake or excessive fluid loss or liver or kidney dysfunctions. This is unsatisfactory for obvious reasons for both the physicians and the patients. Patients must therefore often be adapted to side effects over several weeks as indoor patients in more or less specialized hospitals.

It is the technological problem of the invention to provide an agent and a treatment plan for treating dopaminergic disease states while preventing or at least reducing disturbing side effects, controlling the initial flux rate of the active agent and keeping good control of agent levels in the plasma and effective time.

The invention solves this technological problem by using a dopamine agonist in the form of an agent, comprising at least two discrete compositions, of which one is a transdermal therapeutic system (TTS) containing the dopaminergic agent and another one containing the same dopaminergic agent and suitable for oral and/or parenteral administration, both suitable for the treatment of dopaminergically treatable diseases with the following elements: a) the TTS is continuously applied, b) within the duration of application in a) the composition for oral or parenteral dosage is administered. Phase b) preferably begins 7 days, more preferably 14 days, most preferably 28 days after phase a) was started. The invention involves in this context the use of a dopamine agonist in the form of an agent consisting of at least one spatially discrete composition, of which one is a transdermal therapeutic system (TTS) containing the dopaminergic agent for the treatment of dopaminergically treatable diseases with the following elements: a) the TTS is continuously applied, b) within the duration of application in a), no dopaminergic agent is applied that differs from the dopamine agonistic agent of the TTS.

Continuous application means that a new TTS is applied before the agent level in the plasma drops disturbingly due to the consumption of the previous TTS, such as below the 0.25-fold of the maximum plasma concentration.

The invention is based on the surprising finding that dopaminergically treatable diseases, particularly Parkinson's disease, can be treated better using a single dopaminergic agent that is highly effective and has a short half-life in the plasma, if the combination of the invention is optionally carried out using one of the treatment plans according to the invention. This means it is important that no other agent than the active ingredient of the TTS is used for treating dopaminergic dysfunctions during the treatment period. Lasting or continuous dopaminergic stimulation is achieved using the TTS. It provides agent concentrations in the plasma that can be well controlled or adjusted. The concentration in the plasma can easily be dosed by varying, for example, the effective surface area of the TTS or its size.

Furthermore, a slow increase of the concentration of the active agent in the plasma (over days and weeks) can be achieved by applying the TTS; the benefit is that initial side effects are prevented. Moreover, daily application at relatively early times (e.g. between 6.00 a.m. and 3.00 p.m.), for example, can reliably prevent undesirable overstimulation at night and the risk of psychotic states.

The treatment is supplemented as may be required in advanced stages of a disease by administering oral or parenteral preparations with the same dopaminergic agent. The tablets comprise a preferred tmax of 15 to 120 minutes, particularly preferred of 30 to 60 minutes, and a preferred half-life of 0.5 to 4 hours, particularly preferred 1 to 2 hours. tmax indicates the period of time between oral administration and the buildup of the concentration of the tablet's active agent in the plasma. Half-life is the period of time during which the concentration in the plasma drops by half in the descending portion of the time function. Motoric blockages and akinesia are removed whenever required by such oral administration and the fast extra action as needed.

If oral administrations is started only after starting the continuous application of the TTS, considerable tolerance against dopaminergic side effects has built up and it is no longer required to carry out tedious titrations (sometimes over several months) as would be required for setting up different dopaminergic agents under a combinatory therapy. This makes the treatment particularly well tolerable.

Where indicated—for example, because of the severity of an acute condition (e.g. akinesia or dystonia in the morning or during off periods at other times), the same active agent may be administered parenterally (i.m., i.v., subcutaneously, as contained in the TTS). The same benefits apply in principle as described for oral administration. tmax is typically less than 15 minutes, mostly less than 5 minutes.

Lasting side effects, if unexpected side effects occur, can reliably be prevented due to the short half-life of the active agent. A short-term drop of the agent concentration in the plasma is achieved by just removing the TTS. This is a particular advantage over orally administered, long-term acting agents such as pergolide or cabergoline the side effects of which after an administration or overdosage may last several days.

The invention facilitates relatively high total absorption quantities of the active agent as compared to combinatory therapy where it is highly underdosed to prevent side effects resulting from the complex kinetics and interaction of combining different substances. Thus the invention considerably increases clinical efficacy. This fact combined with better tolerability also allows considerably longer treatment with the respective active agent and avoids the use of levodopa formulations. This is particularly important for younger patients with a high remaining life expectancy as levodopa, the gold standard of dopamine therapy) is known to cause long-term effects resulting in severe and unpredictable dyskinesia and hyperkinesia, which makes the patients eventually dependable on outside help and confines them to bed. Animal experiments have also shown that even short-term levodopa treatment, even at low doses as are common in combinatory therapies, causes lasting priming or sensitization by some kind of inciting mechanism resulting in long-term complications in the motoric and mental dopamine systems. Things being what they are, most patients have to rely on levodopa administrations within the first years of the disease and are exposed to the detrimental long-term disadvantages of levodopa due to the underdosage of active agents administered to avoid side effects.

Despite the relatively high total absorption quantities compared to the underdosage practice that is the state of the art, the actual dosage load can be kept low ($\leq 10$ mg per day, particularly preferred $\leq 5$ mg per day) so that the treatment is relatively independent of any liver or kidney dysfunctions. Potential interaction with other drugs is rather low and predictable as only one active agent is involved in the treatment according to the invention; interaction with the common other Parkinson agents is completely eliminated.

The dopaminergically treatable disease may be a disease from the group consisting of "Parkinson's disease, parkinsonism, restless legs syndrome, and disturbances of the dopaminergic system."

It is preferred when the dopamine agonist with a short half-life is an ergoline derivative of the formula I or a physiologically tolerable salt thereof with an acid,

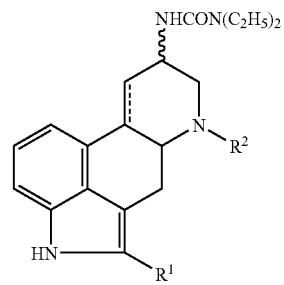

Formula I where

----- is a single or double bond wherein R1 is an H atom or a halogen atom, particularly a bromine atom, and wherein R2 is C1-4 alkyl, particularly methyl.

The list of ergoline derivatives that can be used particularly includes the following: Lisuride, bromolisuride (3-(2-bromo-9,10-didehydro-6-methyl-8α-ergolinyl)-1,1-diethyl urea), terguride (3-(6-methyl-8α-ergolinyl)-1,1-diethyl urea) and proterguride (3-(6-propyl-8α-ergolinyl)-1,1-diethyl urea). However it is preferred when the ergoline derivative is lisuride (3-(9,10-didehydro-6-methyl-8α-ergolinyl)-1,1-diethyl urea) or a physiologically compatible salt thereof with an acid.

Suitable salts of the active ingredients include sulfates, phosphates, maleates, citrates and succinates, especially hydrogen maleate.

The TTS can be applied at various intervals depending on the kinetics of active agent release. It is important that the active agent concentration in the plasma does not show any disturbing variation when the TTS is used continuously. It is preferred that the TTS is applied daily.

The preparation prepared for oral or parenteral administration is preferably administered directly in the event of a dopamine-related malfunction. It may be administered preventively if malfunctions are predictable.

The term "TTS" mostly denotes percutaneously acting but also transmucosal systems. A TTS typically has a sheet-like structure and is attached to an area of the skin. A TTS mostly includes a matrix containing an active ingredient (e.g. in the form of a salt) and/or an active ingredient reservoir, and a diffusion barrier that is permeable to the active ingredient on the skin side of the active ingredient reservoir. The system can optionally be attached to the skin by an additional skin-side adhesive that is permeable to the active ingredient. Alternatively, the matrix and/or diffusion barrier can itself have adhesive properties. And finally a non-adhesive TTS can be attached to the skin using other auxiliary means such as adhesive tapes or bandages. The matrix is a material in which the active ingredient is immobilized. An active agent in an active ingredient reservoir however is not necessarily immobilized, which is why the active ingredient reservoir must be enclosed. The diffusion barrier forms the skin-side portion of this shell. It goes without saying that all other parts of the shell should be as impermeable as possible, including diffusion paths, to the active ingredient. Immobilized means in this context that any uncontrolled active ingredient flow is prevented. However diffusion of an active agent in a matrix and/or through a diffusion barrier is not only possible but intended. The diffusion coefficients eventually determine the active ingredient flux from the TTS into a patient's skin. The dose released into a patient's skin is in first approximation a linear function of the active area of the TTS. The active area is the contact area of those TTS portions that allow active ingredient diffusion.

A TTS designed as described above with lisuride as the active ingredient and its use for treating Parkinson's disease are known in principle from publication WO 92/20339. It specifically describes the effect of propylene glycol lauric acid on the flux, i.e. a considerable increase in flux. A TTS containing lisuride is further known from publication WO 91/00746. The active ingredient in a transdermal patch can of course be formulated in accordance with the pharmaceutical methods known as the state of the art.

It is preferred for the TTS to comprise a pharmaceutical layer containing at least one matrix containing the active ingredient and/or an active ingredient reservoir, and a diffusion barrier that is permeable to the active ingredient on the skin side of the active ingredient reservoir; and an ergoline derivative of the formula I or a salt thereof as an active ingredient.

The matrix and/or diffusion barrier may be selected so that the transdermal flux F through human skin measured as described in Example 1 is in the range from 0.1 to 5.0 $\mu g/cm^2/h$, preferably 0.1 to 4.0 $\mu g/cm^2/h$.

It is preferred to arrange a TTS set as part of a means wherein the set contains a multitude of TTS elements and wherein said elements are configured for releasing different doses. The TTS elements can be separated, each TTS element being configured for a continuously ascending sequence of F ranging from 0.1 to 5 $\mu g/cm^2/h$. It is also conceivable to arrange several TTSs with the same F value in a subgroup wherein the F values of the various subgroups form a continuously ascending sequence and other subgroups comprise constant F values, their value being the maximum of the sequence mentioned above. It is preferred to select F and the active area of the TTS so that a dose in the range from 10 $\mu g$ to 2 mg of active ingredient (such as lisuride) builds up during the day or within 24 hours as from the second day of application, and that this dose subsequently rises in steps. The TTS elements can also have a continuous sequence of different active areas. These may also be divided into subgroups as described above. Suitable according to the invention are also other transdermal forms of application known from the state of the art.

The preparation for oral administration can either be in the form of a tablet, a powder, a capsule or a solution, is formulated using the known state-of-the-art methods as required for the respective form of application, and as a tablet preferably contains 25 to 1000 $\mu g$ of the dopaminergic agent (per tablet), resulting in a dose of 0.075 mg to 5.0 mg per day for lisuride, for example.

The preparation for parenteral administration in the form of an injection or infusion solution is formulated in accordance with known methods and preferably contains 25 to 2000 $\mu g$ of the dopaminergic agent (per ml of solution). For example, the parenteral dose needed to achieve a fast additional effect for lisuride is up to 5.0 mg with a continuous infusion over 24 or 16 hours and from 25 up to 200 $\mu g$ in a bolus injection for a single application.

The TTS can be designed as follows. A covering layer can be arranged on the side of the matrix and/or active ingredient reservoir facing away from the skin. It may be formed by films of polyethylene or polyester. It is typically 10 to 100 microns in thickness. The covering layer may be pigmented, varnished, and/or metal plated to ensure sufficient protection from light. Metal plating involves applying a very thin layer (typically less than 1 micron, mostly in the 10-100 nm range) of a metal such as aluminum to the covering layer. Pigments can be all pigments commonly used for coating including effect pigments as long as these are physiologically harmless. A detachable liner such as a siliconized or fluoropolymer-coated protective film can be provided on the application side.

The matrix and/or diffusion barrier may comprise as their main matrix component a substance selected from the group consisting of "polyacrylate, polyurethane, cellulose ether, silicone, polyvinyl compounds, polyisobutylene compounds, silicate and mixtures of these substances as well as copolymers of these polymeric compounds," preferably polyacrylate. A main matrix component makes up at least 50 percent by weight, e.g. at least 80-90 percent by weight of the matrix (matrix to be understood as the finished layer, i.e. main matrix component(s) with adjuvant(s) and active ingredient(s)). The desired flux is set by selecting the substance depending on the diffusion coefficient of the active ingredient and, if required, by selecting the layer thickness of the matrix in orthogonal direction to the skin surface. Matrix thickness is typically in the range from 10 to 500 microns.

A preferred polyacrylate adhesive as main matrix component is commercially available under the brand name GELVA® multipolymer solution 7881, provided by Monsanto Deutschland GmbH, Dusseldorf. We expressly refer to the product sold under this name and its datasheet in the version of Apr. 23, 1996. Another suitable product is Eudragit® E100 provided by Röhm, Germany.

The polyacrylate adhesives listed above provide an advantageous non-trivial combination of properties, namely optimum flux, good adhesive power, good skin compatibility, and durability.

The diffusion barrier can alternatively comprise as its main barrier component a polymer selected from the group consisting of "cellulose ester, cellulose ether, silicone, polyolefin and mixtures as well as copolymers of these substances." What has been said about the term of the main matrix component above analogously applies to the term of the main barrier component. The diffusion barrier can be a film with a thickness from 10 to 300 microns; the actual film thickness is selected (in conjunction with the diffusion coefficient of the active ingredient in the polymer) according to the desired flux.

The matrix and/or active ingredient reservoir and/or diffusion barrier may contain the common adjuvants used in TTSs. It is preferred to use a penetration-enhancing agent that is preferably selected from the group consisting of "C1-C8 aliphatic, cycloaliphatic and aromatic alcohols, saturated and unsaturated C8-18 fatty alcohols, saturated and unsaturated C8-18 fatty acids, hydrocarbons and hydrocarbon mixtures, fatty acid esters from C3-19 fatty acids and C1-6 alkyl monools, dicarboxylic acid dieesters from C4-8 dicarboxylic acids and C1-6 alkyl monools, and mixtures of these substances. Penetration-enhancing agents improve the flux of the active ingredient through the skin to which the TTS is attached. Examples of the substances listed above are: 1,2-propane diol, menthol, dexpanthenol, benzyl alcohol, lauryl alcohol, isocetyl alcohol, cetyl alcohol, mineral oil, lauric acid, isopalmitic acid, isostearic acid, oleic acid; methyl ester, ethyl ester, 2-hydroxyethyl ester, glycerol ester, propyl ester, isopropyl ester, butyl ester, sec. butyl ester or isobutyl ester of lauric acid, myristic acid, stearic acid, or palmitic acid. Use of dimethyl isosorbide, isopropyl myristate and lauryl alcohol is preferred, use of lauryl alcohol is most preferred. Other adjuvants are, for example, crystallization inhibitors. Suitable crystallization inhibitors are highly dispersed silicon dioxide or macromolecular substances such as polyvinyl pyrrolidone, polyvinyl alcohols, dextrines, dextranes, sterines, bile acids and, in particular, polyvinyl pyrrolidone vinylacetate copolymers such as Kollidon® VA 64.

It goes without saying that the penetration-enhancing agent has to be able to diffuse to a sufficient extent through the matrix or diffusion barrier. If a matrix and lauryl alcohol as an adjuvant are used, it is preferred that the lauryl alcohol makes up 10 to 30 percent by weight, most preferred 15 to 20 percent by weight, of the matrix.

The adjuvants can basically make up from 0 to 50 percent by weight of the matrix. The active ingredient can make up 0.5 to 20 percent by weight, preferably 1 to 10 percent by weight, of the matrix. The sum total of main matrix component, adjuvants and active ingredients is always 100 percent by weight.

The active ingredient dose in a human body carrying a TTS is dependent on the diffusion-related properties of the TTS mentioned above and also on its active surface area on the skin. Active surface area means the area over which the matrix or diffusion barrier comes to rest on the skin. Variation in accordance with the desired dosage will preferably be in a range from 1 to 100 $cm^2$. Within the scope of this invention, a physician can easily set up personalized dose variations for a flux adjusted to the given indication by selecting a suitable patch size. Thus the treatment can easily be adjusted to different body weights, age groups, etc. It is particularly feasible to equip a TTS comprising a (rather large) standard area with subdivision markers for partial doses so that a user can just remove the protective film from a partial area corresponding to the specified dose. The respective subsections can easily be printed on the covering layer.

A transdermal and an oral or parenteral form of application of an active ingredient can easily be offered as one kit for a monotherapy of dopaminergic diseases.

The invention also relates to a combination of a transdermal therapeutic system and an oral and/or parenteral preparation containing one and the same dopamine agonist with a short half-life to produce a pharmaceutical for the treatment of dopaminergic diseases.

The invention will be explained in more detail below based on various non-limiting examples.

EXAMPLE 1

Flux Measurement

A FRANZ flow-through diffusion cell is used for flux measurement. The measuring area is 2 $cm^2$. 4 $cm^2$ of ventral and dorsal skin of a male hairless mouse (MF1 hr/hr Ola/Hsd, provided by Harlan Olac, UK) are used as our skin sample after carefully removing any subcutaneous fatty tissue. A 2 $cm^2$ TTS is applied to the skin sample. The acceptor medium is placed on the opposite side. It is diluted HHBSS (Hepes Hanks Balanced Salt Solution) containing 5.96 g/l of Hepes, 0.35 g/l of $NaHCO_3$ and 0.1 ml/l 10× of HBSS (provided by Gibco, Eggenstein, Del.). Furthermore, 1000 I.U./ml of penicillin (benzylpenicillin potassium salt, provided by Fluka, Neu-Ulm, Del.) are used.

The flux is measured as described below. First, the TTS to be measured is applied to the skin. The skin is mounted in the diffusion cell immediately thereafter. Samples of the acceptor medium are taken at 2-hour intervals between t=0 hrs and t=6 hrs and at 8-hour intervals between t=6 hrs and t=54 hrs. 1 ml of acceptor medium per hour is pumped through the diffusion cell using a peristaltic pump. The temperature of the acceptor medium is controlled using a circulating water bath which keeps the skin at a temperature of 31° C. with an accuracy of 1° C.

The active ingredient concentration in the acceptor medium is determined in accordance with the following specifications using a radioimmunoassay.

Calibration curves: These are constructed using two different methanol solutions of non-radioactive lisuride hydrogen maleate salt, each containing 1 mg/ml. These solutions are individually diluted with BSA buffer (0.041 M of $Na_2HPO_2*2H_2O$, 0.026 M of $KH_2PO_4$, 0.154 M of NaCl, 0.015 M of $NaN_3$, 0.1% (w/v) of BSA, pH 7, supplemented with 0.05% (w/v) of ascorbic acid) to obtain lisuride-free base concentrations in the range from 1000-3.9 pg/0.1 ml. In addition, a sample without active ingredient (0 pg) is used. The calibration samples are analyzed three times. The lisuride concentrations are calculated using the pharmacokinetic PC program RIO 2.5 (other common software may also be used).

Sample preparation: The acceptor medium is diluted with BSA buffer prior to the analysis to set the concentrations to an analyzable range of the calibration curve. 100 µl of diluted sample are directly subjected to radioimmunological analysis.

Antiserum: The antiserum (rabbit) is obtained by immunizing with lisuride-1-succinyl-BSA, an immunogen. The antiserum in the assay is diluted 1:12500.

Tracer: $^3H$-lisuride hydrogen maleate with a specific activity of 4.3 GBq/mg is used.

Incubation: 0.1 ml of BSA buffer with active ingredient, 0.1 ml of tracer solution (ca. 5000 cpm/0.1 ml of BSA buffer) and 0.1 ml of diluted antiserum (1:12500) are added to 0.7 ml of BSA buffer and incubated for 18 hours at 4° C.

Separation: antibody-bound lisuride is separated from free lisuride by adding 0.2 ml of charcoal suspension (1.25% (w/v) and 0.125% (w/v) of dextrane in BSA buffer) and incubation for 30 minutes at 0° C. The charcoal is sedimented by centrifuging for 15 minutes at 3000 g. The supernatant liquid (containing antibody-bound active ingredient) is decanted and subjected to radiometric analysis.

Radiometric analysis: 4 ml of Atomlight (NEN) scintillation cocktail are added to the supernatant. The count is carried out using a WALLAC 1409 or 1410 β-scintillation counter without quench control.

Analysis: The percutaneous skin flux is calculated as follows:

$$F=(C*R)/(A*T),$$

where F is the percutaneous flux [$ng/cm^2/h$], C the active ingredient concentration in the acceptor medium [ng/ml], R the acceptor medium flow [1 ml/h], A the measured area [2 $cm^2$] and T the sample-taking interval [h].

The maximum transdermal active ingredient flux is obtained directly from the data. Mean percutaneous flux values are determined during days 1 and 2 of the experiment based on the cumulative absorbed dose in time intervals t=0-22 and t=22-54.

EXAMPLE 2

Manufacturing of a TTS A 15 mg of Kollidon VA 64 (crystallization inhibitor) are dissolved in 15 mg of isopropanol. Then 5 mg of lisuride are sprinkled in. 80 mg of polyacrylate adhesive (Gelva 7881) are placed in a beaker, and the above suspension is added while rerinsing with 30 mg of isopropanol. The crystal-free wet mix obtained is thoroughly intermixed and spread on a siliconized liner using a 500 micron blade. The product is dried at 60° C. for 20 minutes, and finally a covering layer is laminated onto it.

Flux measurements as described in Example 1 showed an F value of 0.43 on day 1, 0.44 on day 2, and a maximum F value of 0.85 (each in $\mu g/cm^2/h$).

EXAMPLE 3

Manufacturing of a TTS B 12.5 mg of dimethyl isosorbide are suspended with 2 mg of lisuride in 15 mg of isopropanol. 80 mg of polyacrylate adhesive (Gelva 7881) are placed in a beaker, and the above suspension is added while rerinsing with 30 mg of isopropanol. The crystal-free wet mix obtained is thoroughly intermixed and spread on a siliconized liner using a 500 micron blade. The product is dried at 60° C. for 20 minutes, and finally a covering layer is laminated onto it.

Flux measurements as described in Example 1 showed an F value of 0.23 on day 1, 0.28 on day 2, and a maximum F value of 0.50 (each in $\mu g/cm^2/h$).

EXAMPLE 4

Manufacturing of a TTS C 27.2 mg of Kollidon VA 64 (crystallization inhibitor) and 16.3 mg of lauryl alcohol are dissolved at 60° C. Then 2 mg of lisuride are dissolved in this solution at 60° C. 39.38 mg of Eudragit E100, 13.41 mg of Citroflex 4A and 1.71 mg of succinic acid are molten at 150-200° C. The lisuride solution is added after the batch has cooled down to 80° C. The product is spread at 80° C. on a siliconized liner using a 500 micron blade. Then the product is cooled down to 20° C.; optionally, a covering layer may be laminated onto it.

Flux measurements as described in Example 1 showed an F value of 0.90 on day 1, 1.76 on day 2, and a maximum F value of 2.53 (each in $\mu g/cm^2/h$).

EXAMPLE 5

Making a Preparation for Oral Administration

A tablet base composition containing lactose, microcrystalline cellulose, corn starch, crosscarmellose and magnesium stearate in the usual quantitative composition is intermixed with 2000 µg of lisuride per each gram of tablet basis composition and pressed into tablets, each of which containing 200 µg of lisuride.

EXAMPLE 6

Making a Preparation for Parenteral Administration

An injection base solution containing lactose, NaCl and aqua p.i. in the usual quantitative composition is intermixed with 50 µg of lisuride per gram of injection base solution and filled into amber glass ampoules containing 50 µg of lisuride per ml of solution and preferably lyophilized.

EXAMPLE 7

Manufacturing of an Agent According to the Invention

A number of TTSs divided into the four groups as described in Example 2 is put together. The fluxes F of lisuride through human skin of the TTSs of each group comprise are 0.25 $\mu g/cm^2/h$, 0.5 $\mu g/cm^2/h$, 0.75 $\mu g/cm^2/h$ and 1.0 $\mu g/cm^2/h$. At least 7 TTSs are to be in the three groups where F is low. 28 or more TTSs are to be in the group with the highest F. A multitude of tablets from Example 5 and/or a multitude of ampoules from Example 6 is packed with the TTSs compiled in this way. The compilation is accompanied by an instruction sheet that refers to the treatment plan according to the invention.

EXAMPLE 8

Treatment of a Patient with Parkinson's Disease

One TTS from Example 7 per day is applied to a Parkinson's disease patient over a period of 28 days. The area of the TTS remains unchanged for seven consecutive days. The TTSs applied in series of 7 consecutive days increase in area so that there will be a four-step increase in lisuride concentration in the plasma (averaged over a day). The lisuride flux F of the TTSs applied in four steps is 0.25 $\mu g/cm^2/h$, 0.5 $\mu g/cm^2/h$, 0.75 $\mu g/cm^2/h$, and 1.0 $\mu g/cm^2/h$. The daily application of a TTS with an F of 1.0 $\mu g/cm^2/h$ after day 28, i.e. there is no further increase of the dose. Whenever a new TTS is applied, the old one is removed, of course.

After day 28, whenever acute conditions such as severe dystonias occur, a tablet from Example 7 is administered, or the content of an ampoule from Example 7 is injected i.m. Instead, or in addition, a tablet from Example 7 or the content of an ampoule from Example 7 may be administered in the morning for preventive reasons.

The patient will at no time during the treatment show any considerable side effects. The oral or parenteral administrations because of acute conditions are particularly well tolerated, and even after these we did not observe any noticeable disruption of the regular REM sleep.

If against all expectations any disturbing side affects do occur, they can be effectively attenuated by removing the TTS without a replacement, which will soon result in a reduction of agent concentration in the plasma.

The invention claimed is:
1. A method of treating Parkinson's disease, Pakinsonism, and Restless Legs Syndrome, the method comprising the step of administering two or more discrete compositions of a dopamine agonist, wherein said discrete compositions comprise a first composition and a second composition,
wherein said first composition comprises a transdermal therapeutic system (TTS) containing first dopamine agonist and wherein said second composition comprises a second preparation of said first dopamine agonist, wherein said second preparation is selected from the group consisting of an oral preparation of the first dopamine agonist, a parenteral preparation of the first dopamine agonist, and mixtures thereof, wherein the second composition is administered within the duration of the administration of the first composition.

2. The method of claim 1, wherein the first dopamine agonist is an ergoline derivative according to Formula 1 or a physiologically compatible salt thereof,

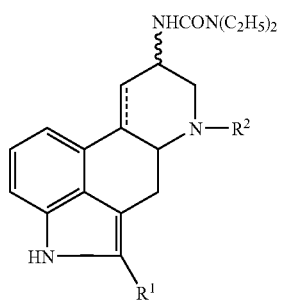

Formula I wherein is a single or double bond wherein $R_1$ is an H atom or a halogen atom, particularly a bromine atom, and wherein $R_2$ is a C1-C4 alkyl.

3. The method of claim 1, wherein the first dopamine agonist is selected from the group consisting of lisuride, pharmaceutically compatible salt lisuride, and mixtures thereof.

4. The method of claim 1, wherein the first dopamine agonist has a half-life of from about 0.5 hours to about 4 hours.

5. The method of claim 1, wherein the TTS comprises a pharmaceutical layer comprising at least one matrix containing the first dopamine agonist.

6. The method of claim 5 wherein the matrix is selected so that the transdermal flux F through human skin is in the range from about 0.1 $\mu g/cm^2/h$ to about 5.0 $\mu g/cm_2/h$.

7. The method of claim 1, wherein the TTS further comprises two or more TTS elements and wherein said TTS elements are configured to release different doses of the first dopamine agonists.

8. The method of claim 1, wherein the second preparation is an oral preparation of the first dopamine agonist, wherein said oral preparation is in tablet form for oral administration, and further wherein the tablet contains from about 25μg to about 500 μg of the first dopamine agonist.

9. The method of claim 1, wherein the second preparation is a parenteral preparation of the first dopamine agonist, wherein said parenteral preparation is selected from the group consisting of an injection solution and an infusion solution, and further wherein the concentration of the first dopamine agonist in said injection solution or said infusion solution is from about 25 μg to about 2000 μg of the first dopamine agonist per ml of solution.

10. A pharmaceutical combination for the treatment of Parkinson's disease, Pakinsonism, and Restless Legs Syndrome the combination comprising a transdermal therapeutic system containing a first dopamine agonist and a second preparation of said first dopamine agonist, wherein said second preparation is selected from the group consisting of an oral preparation of the first dopamine agonist, a parenteral preparation of the first dopamine agonist, and mixtures thereof, and wherein the first dopamine agonist has a short half-life.

11. The method of claim 5, wherein the pharmaceutical layer further comprises a diffusion barrier that is permeable to said first dopamine agonist, wherein said diffusion barrier is on the skin side of the matrix.

12. The method of claim 5 or claim 11, wherein the matrix further comprises a penetration-enhancing agent, wherein said penetration-enhancing agent is selected from the group consisting of: 1,2-propane diol, menthol, dexpanthenol, benzyl alcohol, lauryl alcohol, isocetyl alcohol, cetyl alcohol, mineral oil, lauric acid, isopalmitic acid, isostearic acid, oleic acid; methyl ester, ethyl ester, 2-hydroxyethyl ester, glycerol ester, propyl ester, isopropyl ester, butyl ester, sec. butyl ester of lauric acid, isobutyl ester of lauric acid, myristic acid, stearic acid and palmitic acid.

13. The method of claim 5 or claim 11, wherein the matrix further comprises a penetration-enhancing agent, wherein said penetration-enhancing agent is selected from the group consisting of: dimethyl isosorbide, isopropyl myristate and lauryl alcohol.

14. The method of claim 5 or claim 11, wherein the matrix further comprises a penetration-enhancing agent, wherein said penetration-enhancing agent is lauryl alcohol.

15. The method of claim 1, wherein the TTS comprises a pharmaceutical layer comprising an active ingredient reservoir containing the first dopamine agonist and a diffusion barrier that is permeable to said first dopamine agonist, wherein said diffusion barrier is on the skin side of the active ingredient reservoir.

16. The method of claim 11 or claim 15, wherein the diffusion barrier is selected so that the transdermal flux F through human skin is in the range from about 0.1 $\mu g/cm^2/h$ to about 5.0 $\mu g/cm^2/h$.

17. The method of claim 15, wherein the active ingredient reservoir and the diffusion barrier are selected so that the transdermal flux F through human skin is in the range from about 0.1 $\mu g/cm^2/h$ to about 5.0 $\mu g/cm^2/h$.

18. The method of claim 15, wherein the diffusion barrier further comprises a main barrier component, wherein said main barrier component is substance selected from the group consisting of a polyacrylate, a polyurethane, a cellulose ether, a silicone, a polyvinyl compound, a polyisobutylene compound, a silicate, copolymers of these substances, and mixtures thereof.

19. The method of claim 15, wherein the active ingredient reservoir further comprises a penetration-enhancing agent, wherein the penetration-enhancing agent is selected from the group consisting of: a C1-C8 aliphatic alcohol, a cycloaliphatic alcohol, an aromatic alcohol, a saturated C8-18 fatty alcohol, an unsaturated C8-18 fatty acid, a hydrocarbon, a hydrocarbon mixture, a fatty acid ester from C3-19 fatty acids and C1-6 alkyl monools, a dicarboxylic acid diester from C4-8 dicarboxylic acids and C1-6 alkyl monools, and mixtures thereof.

20. The method of claim 11 or claim 15, wherein the diffusion barrier further comprises a penetration-enhancing agent, wherein the penetration-enhancing agent is selected from the group consisting of: a C1-C8 aliphatic alcohol, a cycloaliphatic alcohol, an aromatic alcohol, a saturated C8-18 fatty alcohol, an unsaturated C8-18 fatty acid, a hydrocarbon, a hydrocarbon mixture, a fatty acid ester from C3-19 fatty acids and C1-6 alkyl monools, a dicarboxylic acid diester from C4-8 dicarboxylic acids and C1-6 alkyl monools, and mixtures thereof.

21. The method of claim 11 or claim 15, wherein the active ingredient reservoir further comprises a penetration-enhancing agent, wherein said penetration-enhancing agent is selected from the group consisting of: 1,2-propane diol, menthol, dexpanthenol, benzyl alcohol, lauryl alcohol, isocetyl alcohol, cetyl alcohol, mineral oil, lauric acid, isopalmitic acid, isostearic acid, oleic acid; methyl ester, ethyl ester, 2-hydroxyethyl ester, glycerol ester, propyl ester, isopropyl ester, butyl ester, sec. butyl ester of laurie acid, isobutyl ester of lauric acid, myristic acid, stearic acid and palmitic acid.

22. The method of claim 15, wherein the active ingredient reservoir further comprises a penetration-enhancing agent, wherein said penetration-enhancing agent is selected from the group consisting of: dimethyl isosorbide, isopropyl myristate and lauryl alcohol.

23. The method of claim 15, wherein the active ingredient reservoir further comprises a penetration-enhancing agent, wherein said penetration-enhancing agent is lauryl alcohol.

24. The method of claim 11 or claim 15, wherein the diffusion barrier further comprises a penetration-enhancing agent, wherein said penetration-enhancing agent is selected from the group consisting of: 1,2-propane diol, menthol, dexpanthenol, benzyl alcohol, lauryl alcohol, isocetyl alcohol, cetyl alcohol, mineral oil, lauric acid, isopalmitic acid, isostearic acid, oleic acid; methyl ester, ethyl ester, 2-hydroxyethyl ester, glycerol ester, propyl ester, isopropyl ester, butyl ester, sec. butyl ester of laurie acid, isobutyl ester of lauric acid, myristic acid, stearic acid and palmitic acid.

25. The method of claim 11 or claim 15, wherein the diffusion barrier further comprises a penetration-enhancing agent, wherein said penetration-enhancing agent is selected from the group consisting of: dimethyl isosorbide, isopropyl myristate and lauryl alcohol.

26. The method of claim 11 or claim 15, wherein the diffusion barrier further comprises a penetration-enhancing agent, wherein said penetration-enhancing agent is lauryl alcohol.

27. The method of claim 1, wherein the TTS further comprises two or more TTS elements and wherein each TTS element is separated from the other and located in a different area of the TTS.

28. The method of claim 1, wherein the TTS further comprises two or more TTS elements and wherein said TTS elements are configured to provide a continuous ascending sequence of flux F values.

29. The method of claim 1, wherein the TTS further comprises two or more TTS elements and wherein said TTS elements are configured to provide a stepwise sequence of flux F values.

30. The method of claim 5 or claim 11, wherein the matrix is selected so that the transdermal flux F through human skin is in the range from about 0.1 $\mu g/cm^2/h$ to about 5.0 $\mu g/cm^2/h$.

31. The method of claim 11, wherein the matrix and the diffusion barrier are selected so that the transdermal flux F through human skin is in the range from about 0.1 $\mu g/cm^2/h$ to about 5.0 $\mu g/cm^2/h$.

32. The method of claim 1, wherein the first dopamine agonist has a half-life of from about 1 hour to about 2 hours.

33. The method of claim 5 or claim 15, wherein the TTS further comprises a covering layer, and wherein the covering layer is located on the side of the matrix or active ingredient reservoir that faces away from the skin.

34. The method of claim 5 or claim 11 wherein the matrix further comprises a main matrix component, wherein said main matrix component is a substance selected from the group consisting of a polyacrylate, a polyurethane, a cellulose ether, a silicone, a polyvinyl compound, a polyisobutylene compound, a silicate, copolymers of these substances, and mixtures thereof.

35. The method of claim 11 or claim 15, wherein the diffusion barrier further comprises a main barrier component, wherein said main barrier component is a substance selected from the group consisting of a cellulose ester, a cellulose ether, a silicone, a polyolefin, copolymers of these substances and mixtures thereof.

36. The method of claim 5 or claim 11 wherein the matrix further comprises a penetration-enhancing agent, wherein the penetration-enhancing agent is selected from the group consisting of a C1-C8 aliphatic alcohol, a cycloaliphatic alcohol, an aromatic alcohol, a saturated C8-18 fatty alcohol, an unsaturated C8-1 8 fatty acid, a hydrocarbon, a hydrocarbon mixture, a fatty acid ester from C3-19 fatty acids and C 1-6 alkyl monools, a dicarboxylic acid diester from C4-8 dicarboxylic acids and C1-6 alkyl monools, and mixtures thereof.

* * * * *